United States Patent [19]

Yuan

[11] Patent Number: 5,760,225

[45] Date of Patent: Jun. 2, 1998

[54] CERTAIN PYRAZOLE DERIVATIVES AS CORTICOTROPIN-RELEASING FACTOR RECEPTOR $CRF_1$ SPECIFIC LIGANDS

[75] Inventor: Jun Yuan, Clinton, Conn.

[73] Assignee: Neurogen Corporation, Branford, Conn.

[21] Appl. No.: 751,107

[22] Filed: Nov. 15, 1996

[51] Int. Cl.$^6$ .................. C07D 401/06; C07D 413/06
[52] U.S. Cl. .................. 544/140; 544/371; 546/146; 546/148; 546/211; 548/374.1; 548/375.1
[58] Field of Search .................. 544/140; 546/148; 548/374.1, 375.1

[56] References Cited

FOREIGN PATENT DOCUMENTS

| | | |
|---|---|---|
| 210 265 | 6/1984 | Germany. |
| WO 94/13643 | 6/1994 | WIPO. |
| WO 94/13644 | 6/1994 | WIPO. |
| WO 94/13661 | 6/1994 | WIPO. |
| WO 96/01254 | 1/1996 | WIPO. |

*Primary Examiner*—Robert W. Ramsuer
*Attorney, Agent, or Firm*—McDonnell Boehnen Hulbert & Berghoff

[57] ABSTRACT

Disclosed are compounds that are highly selective partial agonists or antagonists at human $CRF_1$ receptors that are useful in the diagnosis and treatment of treating stress related disorders such as post traumatic stress disorder (PTSD) as well as depression, headache and anxiety. The compounds have the formula

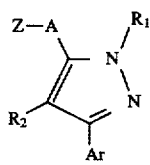

or the pharmaceutically acceptable salts thereof wherein Ar, $R_1$, $R_2$, A, and Z are various organic and inorganic substituents.

25 Claims, No Drawings

CERTAIN PYRAZOLE DERIVATIVES AS CORTICOTROPIN-RELEASING FACTOR RECEPTOR $CRF_1$ SPECIFIC LIGANDS

BACKGROUND OF THE INVENTION

1. Field of the Invention

This invention relates to certain pyrazole derivatives which selectively bind to corticotropin-releasing factor (CRF) receptors. This invention also relates to pharmaceutical compositions comprising such compounds. It further relates to the use of such compounds in treating stress related disorders such as post traumatic stress disorder (PTSD) as well as depression, headache and anxiety.

2. Description Of The Related Art

A variety of pyrazoles have been described in the prior art. International Patent Application Publication No.WO96/01254 (Jan. 18, 1996) discloses certain pyrazole derivatives as herbicides. International Patent Application Publication No. WO94/13643 (Jun. 23, 1994 ) discloses certain pyrazoles and pyrazolopyrimidines as CRF antagonists. International Patent Application Publication No. WO94/13644 (Jun. 23, 1994) and International Patent Application Publication No. WO94/13661 (Jun. 23, 1994) also disclose certain substituted pyrazoles which have CRF antagonistic activities. German Patent DD210265 (Jun. 6, 1984) discloses certain pyrazoles as xanthine oxidase inhibitors.

SUMMARY OF THE INVENTION

This invention provides novel compounds of Formula I which interact with CRF receptors.

The invention provides pharmaceutical compositions comprising compounds of Formula I. It further relates to the use of such compounds in treating stress related disorders such as post traumatic stress disorder (PTSD) as well as depression, headache and anxiety. Accordingly, a broad embodiment of the invention is directed to a compound of Formula I:

wherein

Ar is phenyl, 1- or 2-naphthyl, 2-, 3-, or 4-pyridinyl, 2- or 3-thienyl, 4- or 5-pyrimidinyl, mono, disubstituted, or trisubstituted with halogen, hydroxy, $C_1-C_6$ alkyl, $C_1-C_6$ alkoxy with the proviso that at least one of the positions on Ar ortho to the point of attachment to the pyrazole ring is substituted;

A is $CH_2$ or C=O;

$R_1$ is hydrogen, $C_1-C_6$ alkyl;

$R_2$ is hydrogen, $C_1-C_6$ alkyl, or $C_1-C_6$ alkenyl;

Z is a group of the formula

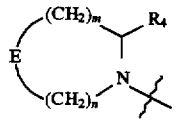

where $R_4$ is hydrogen, $C_1-C_6$ alkyl, or $(C_1-C_6)$alkyl-W—$R_8$, where W is O, S NH, or $N(C_1-C_6)$ alkyl, and $R_8$ is hydrogen or $C_1-C_6$ alkyl;

m is 0, 1 or 2;

n is 0, 1 or 2; and

E represents $CHR_5$ where $R_5$ is hydrogen, $C_1-C_6$ alkyl, $C_1-C_6$ alkoxy, hydroxy, halogen, or trifluoromethyl, phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds;

or

E is a group of the formula

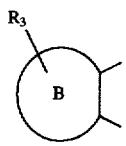

where $R_3$ is hydrogen, $C_1-C_6$ alkyl, $C_1-C_6$ alkoxy, hydroxy, halogen, or trifluoromethyl; and the B ring is phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds; or Z is —$NR_6R_7$ where $R_6$ and $R_7$ are the same or different and represent hydrogen, $C_1-C_6$ alkyl, $(C_1-C_6)$alkyl-Y—$R_9$, wherein Y is O, S NH, $N(C_1-C_6$ alkyl), and $R_9$ is hydrogen or $C_1-C_6$ alkyl; or aryl$(C_1-C_6)$alkyl, wherein aryl is phenyl, 1- or 2-naphthyl, 2-, 3-, or 4-pyridinyl, 2- or 3-thienyl or 2-, 4-, or 5-pyrimidinyl, each of which is mono- or disubstituted with halogen, hydroxy, $(C_1-C_6)$alkyl, $(C_1-C_6)$ alkoxy; or $R_6$ and $R_7$ taken together represent —$(CH_2)_n$—Y—$(CH_2)_m$— wherein n is 2, or 3, Y is $CH_2$, O, S or $NR_6$, wherein $R_6$ is $C_1-C_6$ alkyl, phenyl, 2-, 3-, or 4-pyridinyl, 2- or 3-thienyl, or 2-, 4-, or 5-pyrimidinyl, and m is 1, 2 or 3.

These compounds are highly selective partial agonists or antagonists at CRF receptors and are useful in the diagnosis and treatment of stress related disorders such as post traumatic stress disorder (PTSD) as well as depression and anxiety.

DETAILED DESCRIPTION OF THE INVENTION

In addition to the compounds of Formula I above, the invention provides compounds encompassed by Formula IIA:

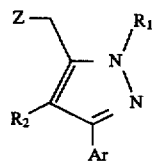

wherein

Ar is phenyl, 1- or 2-naphthyl, 2-, 3-, or 4-pyridinyl, 2- or 3-thienyl, 4- or 5-pyrimidinyl, mono, disubstituted, or trisubstituted with halogen, hydroxy, $C_1-C_6$ alkyl, $C_1-C_6$ alkoxy with the proviso that at least one of the positions on Ar ortho to the point of attachment to the pyrazole ring is substituted;

$R_1$ is hydrogen, $C_1-C_6$ alkyl;

$R_2$ is hydrogen, $C_1-C_6$ alkyl, or $C_1-C_6$ alkenyl;

3

Z is a group of the formula

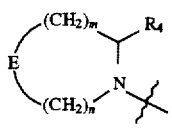

where $R_4$ is hydrogen, $C_1$–$C_6$ alkyl, or $(C_1$–$C_6$)alkyl-W—$R_8$, where W is O, S NH, or $N(C_1$–$C_6)$ alkyl, and $R_8$ is hydrogen or $C_1$–$C_6$ alkyl;

m is 0, 1 or 2;

n is 0, 1 or 2; and

E represents $CHR_5$ where $R_5$ is hydrogen, $C_1$–$C_6$ alkyl, $C_1$–$C_6$ alkoxy, hydroxy, halogen, or trifluoromethyl, phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds;
or E is a group of the formula

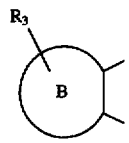

where $R_3$ is hydrogen, $C_1$–$C_6$ alkyl, $C_1$–$C_6$ alkoxy, hydroxy, halogen, or trifluoromethyl; and the B ring is phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds; or Z is —$NR_6R_7$
where $R_6$ and $R_7$ are the same or different and represent hydrogen, $C_1$–$C_6$ alkyl, $(C_1$–$C_6)$alkyl-Y—$R_9$, wherein Y is O, S NH, $N(C_1$–$C_6$ alkyl), and $R_9$ is hydrogen or $C_1$–$C_6$ alkyl; or aryl($C_1$–$C_6$)alkyl, wherein aryl is phenyl, 1- or 2-naphthyl, 2-, 3-, or 4-pyridinyl, 2- or 3-thienyl or 2-, 4-, or 5-pyrimidinyl, each of which is mono- or disubstituted with halogen, hydroxy, $(C_1$–$C_6)$alkyl, $(C_1$–$C_6)$ alkoxy; or $R_6$ and $R_7$ taken together represent —$(CH_2)_n$—Y—$(CH_2)_m$— wherein n is 2, or 3, Y is $CH_2$, O, S or $NR_6$, wherein $R_6$ is $C_1$–$C_6$ alkyl, phenyl, 2-, 3-, or 4-pyridinyl, 2- or 3-thienyl, or 2-, 4-, or 5-pyrimidinyl, and m is 1, 2 or 3.

Preferred compounds of formula IIA are those where Z is 1,2,3,4-tetrahydroisoquinoline, 3-hydroxymethyl-1,2,3,4-tetrahydroisoquinoline or 3-methoxymethyl-1,2,3,4-tetrahydroisoquinoline.

The invention also provides compounds of formula IIB:

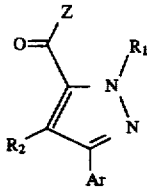

IIB wherein

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with

4 the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl;

Z is a group of the formula

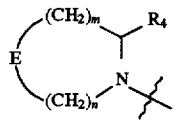

where $R_4$ is hydrogen, $C_1$–$C_6$alkyl, or $(C_1$–$C_6$ )alkyl-W—$R_8$, where W is O, NH, or $N(C_1$–$C_6)$ alkyl, and $R_8$ is hydrogen or $C_1$–$C_6$ alkyl;

m is 0, 1 or 2;

n is 0, 1 or 2; and

E represents $CHR_5$ where $R_5$ is hydrogen, $C_1$–$C_6$ alkyl, $C_1$–$C_6$ alkoxy, hydroxy, halogen, trifluoromethyl, phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds;

or

E is a group of the formula

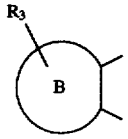

where $R_3$ is hydrogen, $C_1$–$C_6$ alkyl, $C_1$–$C_6$ alkoxy, hydroxy, halogen, or trifluoromethyl; and the B ring is phenyl, naphthyl, pyridinyl, pyrimidinyl, or a saturated 5- or 6-membered ring or a partially unsaturated ring having one or two double bonds; or Z is —$NR_6R_7$ where $R_6$ and $R_7$ are the same or different and represent hydrogen, $C_1$–$C_6$ alkyl, $(C_1$–$C_6)$alkyl-Y—$R_9$, wherein Y is O, S NH, $N(C_1$–$C_6$ alkyl), and $R_9$ is hydrogen or $C_1$–$C_6$ alkyl; or aryl($C_1$–$C_6$)alkyl, wherein aryl is phenyl, 1- or 2-naphthyl, 2-, 3-, or 4-pyridinyl, 2- or 3-thienyl or 2-, 4-, or 5-pyrimidinyl, each of which is mono- or disubstituted with halogen, hydroxy, $(C_1$–$C_6)$alkyl, $(C_1$–$C_6)$alkoxy; or $R_6$ and $R_7$ taken together represent —$(CH_2)_n$—Y—$(CH_2)_m$— wherein n is 2, or 3, Y is $CH_2$, O, S or $NR_6$, wherein $R_6$ is $C_1$–$C_6$ alkyl, phenyl, 2-, 3-, or 4-pyridinyl, 2- or 3-thienyl, or 2-, 4-, or 5-pyrimidinyl, and m is 1, 2 or 3.

Preferred compounds of formula IIB are those where Z is 1,2,3,4-tetrahydroisoquinoline, 3-hydroxymethyl-1,2,3,4-tetrahydroisoquinoline or 3-methoxymethyl-1,2,3,4-tetrahydroisoquinoline.

The invention provides compounds of formula III

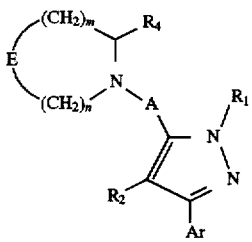

III wherein

A is methylene or carbonyl;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl;

$R_4$ is hydrogen, $C_1$–$C_6$alkyl, or $(C_1$ –$C_6$ )alkyl-W—$R_8$, where W is O, NH, or $N(C_1$–$C_6)$ alkyl, and $R_8$ is hydrogen or $C_1$–$C_6$ alkyl;

m is 0, 1 or 2;

n is 0, 1 or 2; and

E represents $CHR_5$ where $R_5$ is hydrogen, $C_1$–$C_6$ alkyl, $C_1$–$C_6$ alkoxy, hydroxy, halogen, trifluoromethyl, phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds; or E is a group of the formula

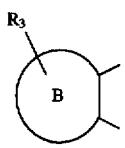

where $R_3$ is hydrogen, $C_1$–$C_6$ alkyl, $C_1$–$C_6$ alkoxy, hydroxy, halogen, or trifluoromethyl; and the B ring is phenyl, naphthyl, pyridinyl, pyrimidinyl, or a saturated 5- or 6-membered ring or a partially unsaturated ring having one or two double bonds.

Preferred compounds of formula III are those where Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted. More preferred compounds of Formula III are those where $R_1$ and $R_2$ are independently hydrogen or lower alkyl, most preferably hydrogen or $C_1$–$C_3$ alkyl; and Ar is phenyl that is trisubstituted with $C_1$–$C_6$ alkyl, with the proviso that at least one of the positions on the phenyl group ortho to the point of attachment to the pyrazole ring is substituted. Most preferred compounds of Formula III are those where $R_1$ and $R_2$ are independently $C_1$–$C_3$ alkyl; and Ar is phenyl that is trisubstituted in the 1, 3, and 5 positions (para and both ortho postions relative to the point of attachment to the pyrazole ring) with $C_1$–$C_3$ alkyl, most preferably methyl.

The invention provides compounds of formula IV

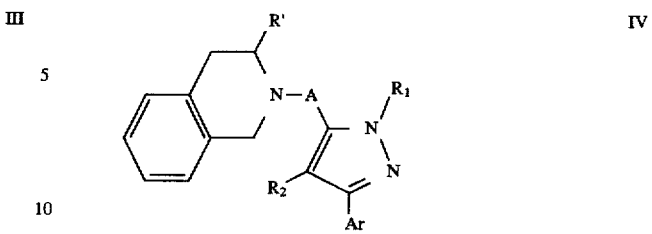

IV wherein

A is carbonyl or methylene;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl; and

R' is hydrogen, hydroxy $C_1$–$C_6$ alkyl, or $C_1$–$C_6$ alkoxy $C_1$–$C_6$ alkyl.

Preferred compounds of formula IV are those where Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted. More preferred compounds of Formula IV are those where $R_1$ and $R_2$ are independently hydrogen or lower alkyl, most preferably hydrogen or $C_1$–$C_3$ alkyl; and Ar is phenyl that is trisubstituted with $C_1$–$C_6$ alkyl, with the proviso that at least one of the positions on the phenyl group ortho to the point of attachment to the pyrazole ring is substituted. Most preferred compounds of Formula IV are those where R' is represents hydrogen, methoxymethyl, or hydroxymethyl, $R_1$ and $R_2$ are independently $C_1$–$C_3$ alkyl; and Ar is phenyl that is trisubstituted in the 1, 3, and 5 positions (i.e., the para and both ortho positions relative to the point of attachment to the pyrazole ring) with $C_1$–$C_3$ alkyl, most preferably methyl.

Other preferred hydroxy alkyl or alkoxy alkyl groups at R' in Formula IV are hydroxymethyl and methoxymethyl. Preferred compounds of formula IV are those where Z is 1,2,3,4-tetrahydroisoquinoline, 3-hydroxymethyl-1,2,3,4-tetrahydroisoquinoline or 3-methoxymethyl-1,2,3,4-tetrahydroisoquinoline.

The invention further provides compounds of formula V

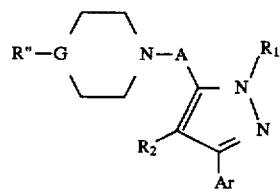

wherein

A is methylene or carbonyl;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl;

G is CH or N; and

R" represents $C_1$–$C_6$ alkyl or a phenyl group optionally substituted with $C_1$–$C_6$ alkyl, $C_1$–$C_6$ alkoxy, hydroxy, halogen, trifluoromethyl, or phenyl.

Preferred compounds of formula V are those where G is nitrogen, Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted. More preferred compounds of Formula V are those where G is nitrogen, $R_1$ and $R_2$ are independently hydrogen or lower alkyl, most preferably hydrogen or $C_1$–$C_3$ alkyl; and Ar is phenyl that is trisubstituted with $C_1$–$C_6$ alkyl, with the proviso that at least one of the positions on the phenyl group ortho to the point of attachment to the pyrazole ring is substituted. Most preferred compounds of Formula V are those where G is nitrogen, R" is methyl or phenyl, $R_1$ and $R_2$ are independently $C_1$–$C_3$ alkyl; and Ar is phenyl that is trisubstituted in the 1, 3, and 5 positions (para and both ortho postions relative to the point of attachment to the pyrazole ring) with $C_1$–$C_3$ alkyl, most preferably methyl. Other most preferred compounds of Formula V are those where A is methylene and G is nitrogen, R" is methyl or phenyl, $R_1$ and $R_2$ are independently $C_1$–$C_3$ alkyl; and Ar is phenyl that is trisubstituted in the 1, 3, and 5 positions (para and both ortho postions relative to the point of attachment to the pyrazole ring) with $C_1$–$C_3$ alkyl, most preferably methyl.

The invention provides compounds of formula VI

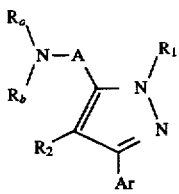

VI wherein

A is methylene or carbonyl;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, or $C_1$–$C_6$ alkyl;

$R_2$ is hydrogen, $C_1$–$C_6$ alkyl, or $C_1$–$C_6$ alkenyl;

$R_a$ represents hydrogen or $C_1$–$C_6$ alkyl; and $R_b$ represents $C_1$–$C_6$ alkyl or a phenyl group optionally substituted with $C_1$–$C_6$ alkyl, $C_1$–$C_6$ alkoxy, hydroxy, halogen, or trifluoromethyl.

Preferred compounds of formula VI are those where Ar is phenyl that is mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted. More preferred compounds of Formula VI are those where $R_1$ and $R_2$ are independently hydrogen or lower alkyl, most preferably hydrogen or $C_1C_3$ alkyl; and Ar is phenyl that is trisubstituted with $C_1$–$C_6$ alkyl, with the proviso that at least one of the positions on the phenyl group ortho to the point of attachment to the pyrazole ring is substituted. Most preferred compounds of Formula V are those where $R_a$ is hydrogen or lower alkyl, most preferably methyl, $R_b$ is optionally substituted phenyl, $R_1$ and $R_2$ are independently $C_1$–$C_3$ alkyl; and Ar is phenyl that is trisubstituted in the 1, 3, and 5 positions (para and both ortho postions relative to the point of attachment to the pyrazole ring) with $C_1$–$C_3$ alkyl, most preferably methyl.

Representative compounds of the present invention, which are encompassed by Formula I, include, but are not limited to the compounds in Table I and their pharmaceutically acceptable salts. Non-toxic pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, HOOC—$(CH_2)_n$—COOH where n is 0–4, and the like. Those skilled in the art will recognize a wide variety of non-toxic pharmaceutically acceptable addition salts.

The present invention also encompasses the acylated prodrugs of the compounds of Formula I. Those skilled in the art will recognize various synthetic methodologies which may be employed to prepare non-toxic pharmaceutically acceptable addition salts and acylated prodrugs of the compounds encompassed by Formula I.

When a compound of formula I is obtained as a mixture of enantiomers these may be separated by conventional methods such as crystallization in the presence of a resolving agent, or chromatography, for example, using a chiral HPLC column.

By the terms ($C_1$–$C_6$)alkyl and lower alkyl is meant straight and branched chain alkyl groups having from 1–6 carbon atoms as well as cyclic alkyl groups such as, for example, cyclopropyl, cyclobutyl, or cyclohexyl. Specific examples of such alkyl groups are methyl, ethyl, propyl, isopropyl, n-butyl, isobutyl, tert-butyl, sec-butyl, neopentyl and n-pentyl. Preferred $C_1$–$C_6$ alkyl groups are methyl, ethyl, propyl, butyl or cyclopropylmethyl.

By the terms ($C_1$–$C_6$)alkoxy and lower alkoxy is meant straight and branched chain alkoxy groups having from 1–6 carbon atoms.

By hydroxy $C_1$–$C_6$ alkyl is meant a $C_1$–$C_6$ alkyl group carrying a terminal hydroxy moiety.

By $C_1$–$C_6$ alkoxy $C_1$–$C_6$ alkyl is meant a group of the formula —$(CH_2)_xO(CH_2)_yCH_3$, where x and y independently represent integers of from 1–6.

By the term $C_1$–$C_6$ alkenyl is meant straight or branched chain hydrocarbon groups having from 1–6 carbon atoms and at least one double bond.

By halogen, halo, or halide is meant fluorine, chlorine, bromine and iodine substituents.

By aryl($C_1$–$C_6$)alkyl is meant aryl groups attached to the parent group by a straight or branched chain alkyl group having 1–6 carbon atoms. The aryl groups include phenyl, 1- or 2-naphthyl, 2-, 3-, or 4-pyridinyl, 2- or 3-thienyl or 2-, 4-, or 5-pyrimidinyl and are optionally substituted with up to two groups selected from halogen, hydroxy, ($C_1$–$C_6$)alkyl, and ($C_1$–$C_6$)alkoxy.

Representative examples of-pyrazoles according to the invention are shown in Table 1 below.

TABLE 1

| Compound No. | |
|---|---|
| 1 | (structure: 1,2,3,4-tetrahydroisoquinoline-CH₂-N=C(Et)-C(=N-N(CH₃)(Et))-mesityl) |
| 2 | (structure: 3-hydroxymethyl-1,2,3,4-tetrahydroisoquinoline-N-CH₂-C(Et)=C(-N(CH₃)N=)-mesityl with HOCH₂ substituent) |
| 3 | (structure: 3-methoxymethyl-1,2,3,4-tetrahydroisoquinoline analog, H₃C—O—CH₂ substituent) |
| 11 | (structure: 1,2,3,4-tetrahydroisoquinolinyl-C(=O)-C(=C(Et))-C(=N-N(CH₃)(Et))-mesityl) |
| 12 | (structure: N-benzyl-N-ethyl amide analog with mesityl and hydrazone group) |
| 15 | (structure: 4-methylpiperazinyl-CH₂-C(CH₃)=C(mesityl)-N=N-(CH₃)(Et)) |
| 16 | (structure: 4-phenylpiperazinyl-CH₂-C(CH₃)=C(mesityl)-N=N(CH₃)(Et)) |

The pharmaceutical utility of compounds of this invention are indicated by the following assay for CRF receptor activity.

Assay for CRF Receptor Binding Activity

CRF receptor binding was performed using a modified version of the assay described by Grigoriadis and De Souza (Biochemical, Pharmacological, and Autoradiographic Methods to Study Corticotropin-Releasing Factor Receptors. *Methods in Neurosciences*, Vol. 5, 1991). Membrane pellets containing CRF receptors were resuspended in 50 mM Tris buffer pH 7.7 containing 10 mM $MgCl_2$ and 2 mM EDTA and centrifuged for 10 minutes at 48000 g. Membranes were washed again and brought to a final concentration of 1500 mg/ml in binding buffer (Tris buffer above with 0.1% BSA, 15 mM bacitracin and 0.01 mg/ml aprotinin.). For the binding assay, 100 ml of the membrane preparation was added to 96 well microtube plates containing 100 ml of 125I-CRF (SA 2200 Ci/mmol, final concentration of 100 pM) and 50 ml of drug. Binding was carried out at room temperature for 2 hours. Plates were then harvested on a Brandel 96 well cell harvester and filters were counted for gamma emissions on a Wallac 1205 Betaplate liquid scintillation counter. Non specific binding was defined by 1 mM cold CRF. $IC_{50}$ values were calculated with the non-linear curve fitting program RS/1 (BBN Software Products Corp., Cambridge, Mass.). The binding affinity for the compounds of formula I expressed as $IC_{50}$ value, generally range from about 0.5 nanomolar (nM) to about 10 micromolar (μM).

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

A representative illustration of methods suitable for the preparation of compounds of the present invention is shown in Scheme I. Those having skill in the art will recognize that the starting materials may be varied and additional steps employed to produce compounds encompassed by the present invention.

Scheme I

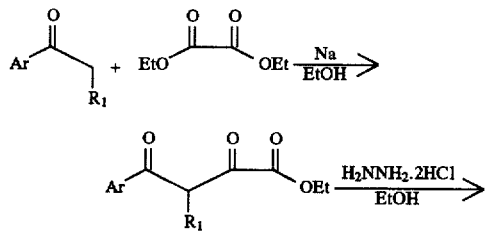

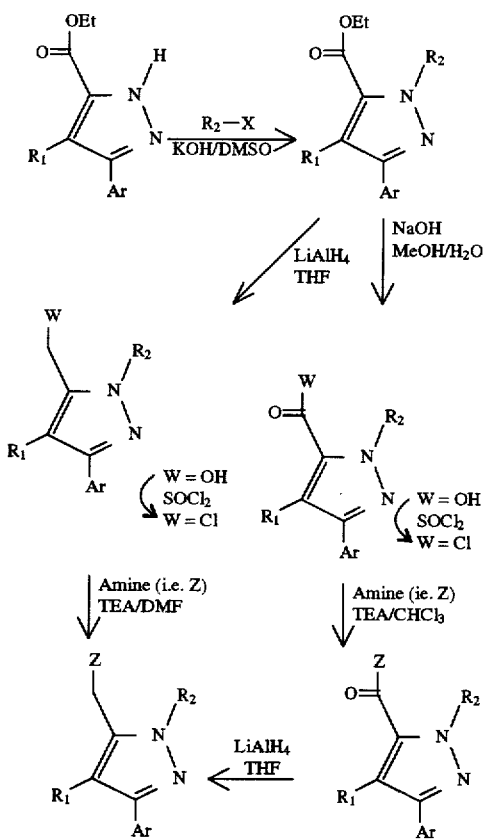

wherein

Ar, $R_1$, $R_2$, and Z are as defined as above for Formula I; and

X is a leaving group, such as, for example, chloride or bromide.

The disclosures in this application of all articles and references, including patents, are incorporated herein by reference.

The invention is illustrated further by the following examples which are not to be construed as limiting the invention in scope or spirit to the specific procedures and compounds described in them.

EXAMPLE 1

A. Ethyl 3-ethyl-2,4-dioxo-4-(2,4,6-trimethylphenyl)butanoate

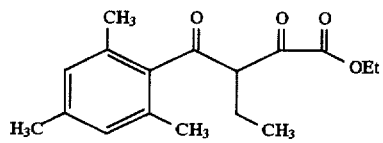

Sodium (1.0 g, 42.1 mmol, spheres) was cautiously added to 25 mL of absolute EtOH with stirring. After the sodium had dissolved, diethyl oxalate (6.0 g, 42.1 mmol) was added dropwise to the resulting solution at 0° C., followed by addition of a solution of 2',4',6'-trimethylbutyrophenone (8 g, 42.1 mmol) in 5 mL of absolute EtOH. The reaction mixture was slowly warmed to 50° C. and stirred overnight. The solvent was then evaporated. The resulting residue was washed with hexane, diluted with water, acidified with 1N HCl, and then extracted with ether. The extracts were washed with brine, dried over Na₂SO₄ and concentrated to give 6.5 g of an oil which was used in the next reaction without further purification.

B. Ethyl 4-ethyl-3-(2,4,6-trimethylphenyl)-1H-pyrazole-5-carboxylate

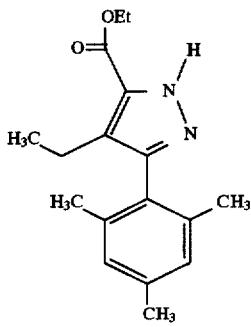

A mixture of ethyl 3-ethyl-2,4-dioxo-4-(2,4,6-trimethylphenyl)butanoate (6.0 g, 20.7 mmol) and hydrazine dihydrochloride (2.17 g, 20.7 mmoL) in 100 mL of EtOH was stirred at 80° C. for 6 hours. The solvent was then removed from the mixture. 200 mL of water was added to the residue and mixture was neutralized by the addition of solid NaHCO₃. The product was extracted into ether. The ether extract was dried over Na₂SO₄ and evaporated to give 5.8 g as an oil which was used in the next reaction without further purification.

C. Ethyl 1,4-diethyl-3-(2,4,6-trimethylphenyl)-1H-pyrazole-5-carboxylate

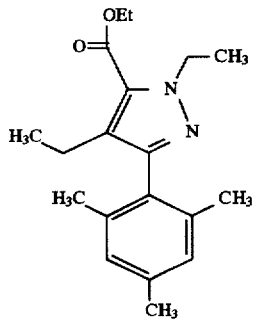

To a red mixture of the product of step B (1.0 g, 3.5 mmol) and powdered KOH (2.0 g) in 50 mL of DMSO was added bromoethane (2.0 mL) at 60° C. The reaction mixture was stirred for 1 hour then poured into ice-water. The resulting mixture was extracted with ether. The ether extract was washed with brine, dried over Na₂SO₄, and concentrated to provide an oil which was comprised of the isomeric pair ethyl 1,4-diethyl-3-(2,4,6-trimethylphenyl)-pyrazole-5-carboxylate and ethyl 1,4-diethyl-5-(2,4,6-trimethylphenyl)-pyrazole-3-carboxylate in a 1:1 mixture. The isomers were separated by column chromatography over silica gel using CH₂Cl₂ as eluent. The faster moving fraction, comprising the titled compound, was collected. Evaporation of the solvent gave about 400 mg of the desired compound as an oil. ¹H NMR (CDCl₃): 0.95 (t, 3H), 1.42 (m, 6H) 2.00 (s, 6H), 2.30 (s, 3H), 2.42 (q, 2H), 4.40 (q, 2H), 4.59 (q, 2H), 6.90 (s, 2H) ppm.

D. 5-Chloromethyl-1,4-diethyl-3-(2,4,6-trimethylphenyl)-1H-pyrazole hydrochloride

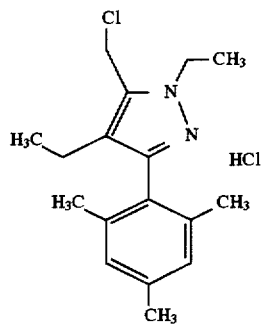

To a solution of the product of step C (320 mg, 1 mmol) in 10 mL of anhydrous THF was added dropwise a solution of LiAlH₄ (3 mL, 1M in THF) at 0° C. After stirring for 2 hours, water was cautiously added. The mixture was then extracted repeatedly with ether. The combined extracts were washed with brine, dried and concentrated. The residue was dissolved in 1 mL of SOCl₂, stirred at 60° C. for 2 hours and evaporated to provide the title compound which was used in the next reaction without further purification.

E. 2-{1-[1,4-Diethyl-3-(2,4,6-trimethylphenyl)-1H-pyrazol-5-yl]methyl}-1,2,3,4-tetrahydroisoquinoline (Compound 1)

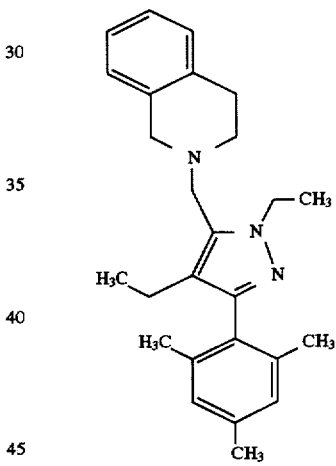

A mixture of the product of step D (from above) and 1,2,3,4-tetrahydroisoquinoline (150 mg, 1.1 mmol) and triethylamine (1 mL) in 5 mL of DMF was heated at 100° C. for 1 hour. The mixture was cooled, diluted with water, basified with 1 N NaOH, and finally extracted with ether. The organic layer was separated, washed with brine, dried over Na₂SO₄ and concentrated to give about 500 mg of the crude compound as an oil. The oil was purified through silica gel column chromatography to give 160 mg of the title compound as an oil. ¹H NMR (CDCl₃): 0.90 (t, 3H), 1.39 (t, 3H), 2.05 (s, 6H), 2.25 (q, 2H), 2.31 (s, 3H), 2.76 (q, 2H), 2.90 (q, 2H), 3.66 (s, 2H), 3.68 (s, 2H), 4.24 (q, 2H), 6.90 (s, 2H), 7.05 (m, 1H), 7.15 (m, 3H)ppm.

The following compounds are prepared essentially according to procedures set forth above in Example 1.

EXAMPLE 2

2-{1-[1,4-Diethyl-3-(2,4,6-trimethylphenyl)-1H-pyrazol-5-yl]-methyl}-3-hydroxymethyl-1,2,3,4-tetrahydroisoquinoline (Compound 2)

EXAMPLE 3

2-{1-[1,4-Diethyl-3-(2,4,6-trimethylphenyl)-1H-pyrazol-5-yl]-methyl}-3-methoxymethyl-1,2,3,4-tetrahydroisoquinoline (Compound 3)

EXAMPLE 4

2-{1-[1-Ethyl-4-methyl-3-(2,4,6-trimethylphenyl)-1H-pyrazol-5-yl]-methyl}-1,2,3,4-tetrahydroisoquinoline

EXAMPLE 5

2-{1-[1-Ethyl-4-methyl-3-(2,4,6-trimethylphenyl)-1H-pyrazol-5-yl]-methyl}-3-hydroxymethyl-1,2,3,4-tetrahydroisoquinoline

EXAMPLE 6

2-{1-[1-Ethyl-4-methyl-3-(2,4,6-trimethylphenyl)-1H-pyrazol-5-yl]-methyl}-3-methoxymethyl-1,2,3,4-tetrahydroisoquinoline

EXAMPLE 7

1-{1-[1-Ethyl-4-methyl-3-(2,4,6-trimethylphenyl)-1H-pyrazol-5-yl]-methyl}-2-hydroxymethyl-piperidine

EXAMPLE 8

2-{1-[4-Methyl-1-propyl-3-(2,4,6-trimethylphenyl)-1H-pyrazol-5-yl]-methyl}-1,2,3,4-tetrahydroisoquinoline

EXAMPLE 9

2-{1-[4-Methyl-1-propyl-3-(2,4,6-trimethylphenyl)-1H-pyrazol-5-yl]-methyl}-3-hydroxymethyl-1,2,3,4-tetrahydroisoquinoline

EXAMPLE 10

2-{1-[4-Methyl-1-propyl-3-(2,4,6-trimethylphenyl)-1H-pyrazol-5-yl]-methyl}-3-methoxymethyl-1,2,3,4-tetrahydroisoquinoline

EXAMPLE 11

2-{[1,4-diethyl-3-(2,4,6-trimethylphenyl)-1H-pyrazol-5-yl]carbonyl}-1,2,3,4-tetrahydroisoquinoline

EXAMPLE 12

N-Ethyl-N-phenylmethyl-1,4-diethyl-3-(2,4,6-trimethylphenyl)-1H-pyrazole-5-carboxamide

EXAMPLE 13

N-Cyclopropylmethyl-N-propyl-1,4-diethyl-3-(2,4,6-trimethylphenyl)-1H-pyrazole-5-carboxamide

EXAMPLE 14

N,N-(2,2-Dimethoxyethyl)-1,4-diethyl-3-(2,4,6-trimethylphenyl)-1H-pyrazole-5-carboxamide

EXAMPLE 15

1-{1-[1-Ethyl-4-methyl-3-(2,4,6-trimethylphenyl)-1H-pyrazol-5-yl]-methyl}-4-methyl-piperazine

EXAMPLE 16

1-{1-[1-Ethyl-4-methyl-3-(2,4,6-trimethylphenyl)-1H-pyrazol-5-yl]-methyl}-4-phenyl-piperazine

EXAMPLE 17

1-{1-[1-Ethyl-4-methyl-3-(2,4,6-trimethylphenyl)-1H-pyrazol-5-yl]-methyl}-morpholine The invention and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

What is claimed is:

1. A compound of the formula:

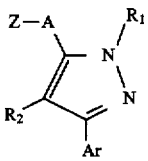

or the pharmaceutically acceptable salts thereof wherein

Ar is phenyl, 1- or 2-naphthyl, 2-, 3-, or 4-pyridinyl, 2- or 3-thienyl, 4- or 5-pyrimidinyl, mono, disubstituted, or trisubstituted with halogen, hydroxy, $C_1$–$C_6$ alkyl, $C_1$–$C_6$ alkoxy with the proviso that at least one of the positions on Ar ortho to the point of attachment to the pyrazole ring is substituted;

A is $CH_2$ or C=O;

$R_1$ is hydrogen, $C_1$–$C_6$ alkyl;

$R_2$ is hydrogen, $C_1$–$C_6$ alkyl, or $C_1$–$C_6$ alkenyl;

Z is a group of the formula

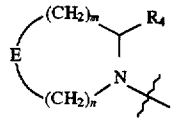

where $R_4$ is hydrogen, $C_1$–$C_6$ alkyl, or ($C_1$–$C_6$)alkyl-W—$R_8$, where W is O, S, NH, or N($C_1$–$C_6$) alkyl, and $R_8$ is hydrogen or $C_1$–$C_6$ alkyl;

m is 0, 1 or 2;

n is 0, 1 or 2; and

E represents $CHR_5$ where $R_5$ is hydrogen, $C_1$–$C_6$ alkyl, $C_1$–$C_6$ alkoxy, hydroxy, halogen, or trifluoromethyl, phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds;

or

E is a group of the formula

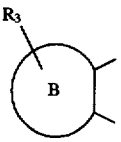

where $R_3$ is hydrogen, $C_1$–$C_6$ alkyl, $C_1$–$C_6$ alkoxy, hydroxy, halogen, or trifluoromethyl; and the B ring is phenyl, naphthyl, pyridinyl, pyrimidinyl, thienyl, imidazolyl, pyrrolyl, pyrazolyl, pyrazinyl, or a saturated 5- or 6-membered ring or a partially unsaturated ring having one or two double bonds; or Z is —$NR_6R_7$ where $R_6$ and $R_7$ are the same or different and represent hydrogen, $C_1$–$C_6$ alkyl, ($C_1$–$C_6$)alkyl-Y—$R_9$, wherein Y is O, S NH, N($C_1$–$C_6$ alkyl), and $R_9$ is hydrogen or $C_1$–$C_6$ alkyl; or aryl($C_1$–$C_6$)alkyl, wherein aryl is phenyl, 1- or 2-naphthyl, 2-, 3-, or 4-pyridinyl, 2- or 3-thienyl or 2-, 4-, or 5-pyrimidinyl, each of which is mono- or disubstituted with halogen, hydroxy, ($C_1$–$C_6$)alkyl, ($C_1$–$C_6$) alkoxy; or $R_6$ and $R_7$ taken together represent —$(CH_2)_n$—Y—$(CH_2)_m$— wherein n is 2, or 3, Y is $CH_2$, O, S or $NR_6$, wherein $R_6$ is $C_1$–$C_6$ alkyl, phenyl, 2-, 3-, or 4-pyridinyl, 2- or 3-thienyl, or 2-, 4-, or 5-pyrimidinyl, and m is 1, 2 or 3.

2. A compound according to claim 1, wherein Z iz 1,2,3,4-tetrahydroisoquinoline, 3-hydroxymethyl-1,2,3,4-tetrahydroisoquinoline or 3-methoxymethyl-1,2,3,4-tetrahydroisoquinoline.

3. A compound of the formula:

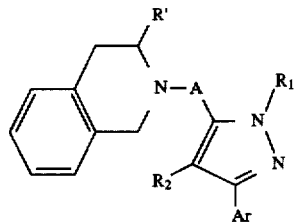

or the pharmaceutically acceptable salts thereof wherein

A is carbonyl or methylene;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl; and

R' is hydrogen, hydroxy $C_1$–$C_6$ alkyl, or $C_1$–$C_6$ alkoxy $C_1$–$C_6$ alkyl.

4. A compound according to claim 3, wherein R' is hydrogen, hydroxymethyl or methoxymethyl.

5. A compound according to claim 3, wherein Ar is phenyl mono-, di-, or trisubstituted with halogen, hydroxy, $C_1$–$C_6$ alkyl, or $C_1$–$C_6$ alkoxy, with the proviso that at least one of the positions on the phenyl group ortho to the point of attachment to the pyrazole ring is substituted.

6. A compound according to claim 3, wherein

R' is represents hydrogen, methoxymethyl, or hydroxymethyl;

$R_1$ and $R_2$ are independently $C_1$–$C_3$ alkyl; and

Ar is phenyl that is trisubstituted in the 1, 3, and 5 positions with $C_1$–$C_3$ alkyl, most preferably methyl.

7. A compound of the formula:

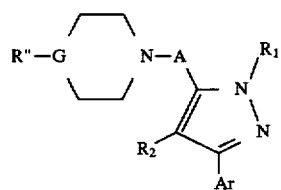

or the pharmaceutically acceptable salts thereof wherein

A is methylene or carbonyl;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl;

G is CH or N; and

R' represents $C_1$–$C_6$ alkyl or a phenyl group optionally substituted with $C_1$–$C_6$ alkyl, $C_1$–$C_6$ alkoxy, hydroxy, halogen, trifluoromethyl, or phenyl.

8. A compound of the formula:

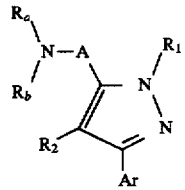

or the pharmaceutically acceptable salts thereof wherein:

A is methylene or carbonyl;

Ar is phenyl, 1- or 2-naphthyl, 2-, 3-, or 4-pyridinyl, 4- or 5-pyrimidinyl, each of which is mono-, di-, or trisubstituted with halogen, hydroxy, $C_1$–$C_6$ alkyl, or $C_1$–$C_6$ alkoxy, with the proviso that at least one of the positions on Ar ortho to the point of attachment to the pyrazole ring is substituted;

$R_1$ is hydrogen, $C_1$–$C_6$ alkyl;

$R_2$ is hydrogen, $C_1$–$C_6$ alkyl, or $C_1$–$C_6$ alkenyl;

$R_a$ represents hydrogen or $C_1$–$C_6$ alkyl; and $R_b$ represents $C_1$–$C_6$ alkyl or a phenyl group optionally substituted with $C_1$–$C_6$ alkyl, $C_1$–$C_6$ alkoxy, hydroxy, halogen, or trifluoromethyl.

9. A compound according to claim 1 which is 2-{1-[1,4-Diethyl-3-(2,4,6-trimethylphenyl)-1H-pyrazol-5-yl]-methyl}-1,2,3,4-tetrahydroisoquinoline.

10. A compound according to claim 1 which is 2-{1-[1,4-Diethyl-3-(2,4,6-trimethylphenyl)-1H-pyrazol-5-yl]-methyl}-3-hydroxymethyl-1,2,3,4-tetrahydroisoquinoline.

11. A compound according to claim 1 which is 2-{1-[1,4-Diethyl-3-(2,4,6-trimethylphenyl)-1H-pyrazol-5-yl]-methyl}-3-methoxymethyl-1,2,3,4-tetrahydroisoquinoline.

12. A compound according to claim 1 which is 2-{1-[1-Ethyl-4-methyl-3-(2,4,6-trimethylphenyl)-1H-pyrazol-5-yl]-methyl}-1,2,3,4-tetrahydroisoquinoline.

13. A compound according to claim 1 which is 2-{1-[1-Ethyl-4-methyl-3-(2,4,6-trimethylphenyl)-1H-pyrazol-5-yl]-methyl}-3-hydroxymethyl-1,2,3,4-tetrahydroisoquinoline.

14. A compound according to claim 1 which is 2-{1-[1-Ethyl-4-methyl-3-(2,4,6-trimethylphenyl)-1H-pyrazol-5-yl]-methyl}-3-methoxymethyl-1,2,3,4-tetrahydroisoquinoline.

15. A compound according to claim 1 which is 1-{1-[1-Ethyl-4-methyl-3-(2,4,6-trimethylphenyl)-1H-pyrazol-5-yl]-methyl}-2-hydroxymethyl-piperidine.

16. A compound according to claim 1 which is 2-{1-[4-Methyl-1-propyl-3-(2,4,6-trimethylphenyl)-1H-pyrazol-5-yl]-methyl}-1,2,3,4-tetrahydroisoquinoline.

17. A compound according to claim 1 which is 2-{1-[4-Methyl-1-propyl-3-(2,4,6-trimethylphenyl)-1H-pyrazol-5-yl]-methyl}-3-hydroxymethyl-1,2,3,4-tetrahydroisoquinoline.

18. A compound according to claim 1 which is 2-{1-[4-Methyl-1-propyl-3-(2,4,6-trimethylphenyl)-1H-pyrazol-5-yl]-methyl}-3-methoxymethyl-1,2,3,4-tetrahydroisoquinoline.

19. A compound according to claim 1 which is 2-{[1,4-diethyl-3-(2,4,6-trimethylphenyl)-1H-pyrazol-5-yl]carbonyl}-1,2,3,4-tetrahydroisoquinoline.

20. A compound according to claim 1 which is N-Ethyl-N-phenylmethyl-1,4-diethyl-3-(2,4,6-trimethylphenyl)-1H-pyrazole-5-carboxamide.

21. A compound according to claim 1 which is N-Cyclopropylmethyl-N-propyl-1,4-diethyl-3-(2,4,6-trimethylphenyl)-1H-pyrazole-5-carboxamide.

22. A compound according to claim 1 which is N,N-(2,2-Dimethoxyethyl)-1,4-diethyl-3-(2,4,6-trimethylphenyl)-1H-pyrazole-5-carboxamide.

23. A compound according to claim 1 which is 1-{1-[1-Ethyl-4-methyl-3-(2,4,6-trimethylphenyl)-1H-pyrazol-5-yl]-methyl}-4-methyl-piperazine.

24. A compound according to claim 1 which is 1-{1-[1-Ethyl-4-methyl-3-(2,4,6-trimethylphenyl)-1H-pyrazol-5-yl]-methyl}-4-phenyl-piperazine.

25. A compound according to claim 1 which is 1-{1-[1-Ethyl-4-methyl-3-(2,4,6-trimethylphenyl)-1H-pyrazol-5-yl]-methyl}-morpholine.

* * * * *